(12) United States Patent
Carpenter et al.

(10) Patent No.: US 6,270,981 B1
(45) Date of Patent: Aug. 7, 2001

(54) METHODS OF SCREENING COMPETITORS OF OB-R BINDING TO SHP-2-SH2 PEPTIDES

(75) Inventors: Laura R. Carpenter, Tuckahoe; Neil Stahl, Carmel; George D. Yancopoulos, Yorktown Heights, all of NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 09/093,814

(22) Filed: Jun. 9, 1998

Related U.S. Application Data

(60) Provisional application No. 60/049,108, filed on Jun. 9, 1997.

(51) Int. Cl.[7] ............................ G01N 33/567; G01N 33/53
(52) U.S. Cl. ............................ 435/7.21; 435/7.1; 435/7.2
(58) Field of Search ........................................ 435/7.1, 7.2

(56) References Cited

U.S. PATENT DOCUMENTS 5,972,621 * 10/1999 Tartaglia et al. ...................... 435/7.1

FOREIGN PATENT DOCUMENTS

| | | | |
|---|---|---|---|
| 9712037 | * | 4/1997 | (WO) . |
| 9725424 | * | 7/1997 | (WO) . |
| 9725425 | * | 7/1997 | (WO) . |
| 9726335 | * | 7/1997 | (WO) . |

OTHER PUBLICATIONS

Kellerer et al, *Diabetologia*, 1997, 40, 1358–62.*
Nakashima et al, *FEBS* 1997, 401 pp. 49–52.*
Darnell, *PNAS* 93, 1996, p. 6221.*
Ghilardi et al, *Mol Endocrin.* 1997 11, pp. 393–99.*
Bjorbaek et al, *JBC* 1997, p. 32680, vol. 272.*
White et al, *JBC* 1997, pp. 4065–4071, vol. 272.*
Devas et al *JBC* 272, 1997, p. 18304.*

* cited by examiner

*Primary Examiner*—Gary L. Kunz
*Assistant Examiner*—Robert S. Landsman
(74) *Attorney, Agent, or Firm*—Linda O. Palladino; Gail M. Kempler

(57) ABSTRACT

The present invention relates to methods for identifying therapeutic agents that enhance the effect of leptin, an adipocyte-derived cytokine that regulates food intake and body weight. The invention further provides for use of agents identified using this assay system to enhance the interaction between leptin and its receptor, OB-R, thereby boosting leptin's weight-reducing effects in obese individuals.

5 Claims, 12 Drawing Sheets

Receptor Construct

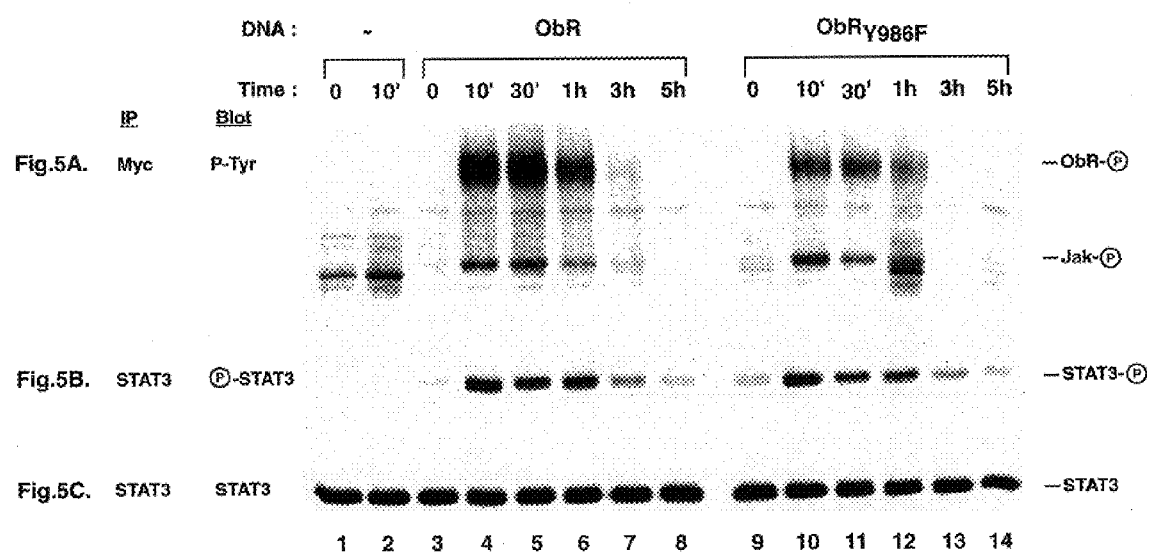

SEQUENCE LISTING

<160> NUMBER OF SEQ ID NOS: 1

<210> SEQ ID NO 1
<211> LENGTH: 1165
<212> TYPE: PRT
<213> ORGANISM: Homo sapiens

<400> SEQUENCE: 1

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg

-continued

```
                20                    25                    30
Phe Lys Leu Ser Cys Met Pro Pro Asn Ser Thr Tyr Asp Tyr Phe Leu
        35                    40                    45

Leu Pro Ala Gly Leu Ser Lys Asn Thr Ser Asn Ser Asn Gly His Tyr
    50                    55                    60

Glu Thr Ala Val Glu Pro Lys Phe Asn Ser Ser Gly Thr His Phe Ser
65                    70                    75                    80

Asn Leu Ser Lys Thr Thr Phe His Cys Cys Phe Arg Ser Glu Gln Asp
                85                    90                    95

Arg Asn Cys Ser Leu Cys Ala Asp Asn Ile Glu Gly Lys Thr Phe Val
                100                   105                   110

Ser Thr Val Asn Ser Leu Val Phe Gln Gln Ile Asp Ala Asn Trp Asn
            115                   120                   125

Ile Gln Cys Trp Leu Lys Gly Asp Leu Lys Leu Phe Ile Cys Tyr Val
        130                   135                   140

Glu Ser Leu Phe Lys Asn Leu Phe Arg Asn Tyr Asn Tyr Lys Val His
145                   150                   155                   160

Leu Leu Tyr Val Leu Pro Glu Val Leu Glu Asp Ser Pro Leu Val Pro
                165                   170                   175

Gln Lys Gly Ser Phe Gln Met Val His Cys Asn Cys Ser Val His Glu
                180                   185                   190

Cys Cys Glu Cys Leu Val Pro Val Pro Thr Ala Lys Leu Asn Asp Thr
            195                   200                   205

Leu Leu Met Cys Leu Lys Ile Thr Ser Gly Gly Val Ile Phe Gln Ser
        210                   215                   220

Pro Leu Met Ser Val Gln Pro Ile Asn Met Val Lys Pro Asp Pro Pro
225                   230                   235                   240

Leu Gly Leu His Met Glu Ile Thr Asp Asp Gly Asn Leu Lys Ile Ser
                245                   250                   255

Trp Ser Ser Pro Pro Leu Val Pro Phe Pro Leu Gln Tyr Gln Val Lys
                260                   265                   270

Tyr Ser Glu Asn Ser Thr Thr Val Ile Arg Glu Ala Asp Lys Ile Val
            275                   280                   285

Ser Ala Thr Ser Leu Leu Val Asp Ser Ile Leu Pro Gly Ser Ser Tyr
        290                   295                   300

Glu Val Gln Val Arg Gly Lys Arg Leu Asp Gly Pro Gly Ile Trp Ser
305                   310                   315                   320

Asp Trp Ser Thr Pro Arg Val Phe Thr Thr Gln Asp Val Ile Tyr Phe
                325                   330                   335

Pro Pro Lys Ile Leu Thr Ser Val Gly Ser Asn Val Ser Phe His Cys
                340                   345                   350

Ile Tyr Lys Lys Glu Asn Lys Ile Val Pro Ser Lys Glu Ile Val Trp
            355                   360                   365

Trp Met Asn Leu Ala Glu Lys Ile Pro Gln Ser Gln Tyr Asp Val Val
        370                   375                   380

Ser Asp His Val Ser Lys Val Thr Phe Phe Asn Leu Asn Glu Thr Lys
385                   390                   395                   400

Pro Arg Gly Lys Phe Thr Tyr Asp Ala Val Tyr Cys Cys Asn Glu His
                405                   410                   415

Glu Cys His His Arg Tyr Ala Glu Leu Tyr Val Ile Asp Val Asn Ile
                420                   425                   430

Asn Ile Ser Cys Glu Thr Asp Gly Tyr Leu Thr Lys Met Thr Cys Arg
        435                   440                   445
```

```
Trp Ser Thr Ser Thr Ile Gln Ser Leu Ala Glu Ser Thr Leu Gln Leu
    450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                485                 490                 495
Glu Cys Ile Phe Gln Pro Ile Phe Leu Leu Ser Gly Tyr Thr Met Trp
                500                 505                 510
Ile Arg Ile Asn His Ser Leu Gly Ser Leu Asp Ser Pro Pro Thr Cys
            515                 520                 525
Val Leu Pro Asp Ser Val Val Lys Pro Leu Pro Pro Ser Ser Val Lys
    530                 535                 540
Ala Glu Ile Thr Ile Asn Ile Gly Leu Leu Lys Ile Ser Trp Glu Lys
545                 550                 555                 560
Pro Val Phe Pro Glu Asn Asn Leu Gln Phe Gln Ile Arg Tyr Gly Leu
                565                 570                 575
Ser Gly Lys Glu Val Gln Trp Lys Met Tyr Glu Val Tyr Asp Ala Lys
                580                 585                 590
Ser Lys Ser Val Ser Leu Pro Val Pro Asp Leu Cys Ala Val Tyr Ala
            595                 600                 605
Val Gln Val Arg Cys Lys Arg Leu Asp Gly Leu Gly Tyr Trp Ser Asn
    610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                645                 650                 655
Glu Lys Asn Val Thr Leu Leu Trp Lys Pro Leu Met Lys Asn Asp Ser
                660                 665                 670
Leu Cys Ser Val Gln Arg Tyr Val Ile Asn His His Thr Ser Cys Asn
            675                 680                 685
Gly Thr Trp Ser Glu Asp Val Gly Asn His Thr Lys Phe Thr Phe Leu
    690                 695                 700
Trp Thr Glu Gln Ala His Thr Val Thr Val Leu Ala Ile Asn Ser Ile
705                 710                 715                 720
Gly Ala Ser Val Ala Asn Phe Asn Leu Thr Phe Ser Trp Pro Met Ser
                725                 730                 735
Lys Val Asn Ile Val Gln Ser Leu Ser Ala Tyr Pro Leu Asn Ser Ser
                740                 745                 750
Cys Val Ile Val Ser Trp Ile Leu Ser Pro Ser Asp Tyr Lys Leu Met
            755                 760                 765
Tyr Phe Ile Ile Glu Trp Lys Asn Leu Asn Glu Asp Gly Glu Ile Lys
    770                 775                 780
Trp Leu Arg Ile Ser Ser Ser Val Lys Lys Tyr Tyr Ile His Asp His
785                 790                 795                 800
Phe Ile Pro Ile Glu Lys Tyr Gln Phe Ser Leu Tyr Pro Ile Phe Met
                805                 810                 815
Glu Gly Val Gly Lys Pro Lys Ile Ile Asn Ser Phe Thr Gln Asp Asp
                820                 825                 830
Ile Glu Lys His Gln Ser Asp Ala Gly Leu Tyr Val Ile Val Pro Val
            835                 840                 845
Ile Ile Ser Ser Ser Ile Leu Leu Leu Gly Thr Leu Leu Ile Ser His
    850                 855                 860
```

| | | | | | | | | | | | |
|---|---|---|---|---|---|---|---|---|---|---|---|
| Gln | Arg | Met | Lys | Lys | Leu | Phe | Trp | Glu | Asp | Val | Pro | Asn | Pro | Lys | Asn |
| 865 | | | | 870 | | | | | 875 | | | | | 880 | |
| Cys | Ser | Trp | Ala | Gln | Gly | Leu | Asn | Phe | Gln | Lys | Pro | Glu | Thr | Phe | Glu |
| | | | | 885 | | | | | 890 | | | | | 895 | |
| His | Leu | Phe | Ile | Lys | His | Thr | Ala | Ser | Val | Thr | Cys | Gly | Pro | Leu | Leu |
| | | | 900 | | | | | 905 | | | | | 910 | | |
| Leu | Glu | Pro | Glu | Thr | Ile | Ser | Glu | Asp | Ile | Ser | Val | Asp | Thr | Ser | Trp |
| | | 915 | | | | | 920 | | | | | 925 | | | |
| Lys | Asn | Lys | Asp | Glu | Met | Met | Pro | Thr | Thr | Val | Val | Ser | Leu | Leu | Ser |
| | 930 | | | | | 935 | | | | | 940 | | | | |
| Thr | Thr | Asp | Leu | Glu | Lys | Gly | Ser | Val | Cys | Ile | Ser | Asp | Gln | Phe | Asn |
| 945 | | | | | 950 | | | | | 955 | | | | | 960 |
| Ser | Val | Asn | Phe | Ser | Glu | Ala | Glu | Gly | Thr | Glu | Val | Thr | Tyr | Glu | Ala |
| | | | | 965 | | | | | 970 | | | | | 975 | |
| Glu | Ser | Gln | Arg | Gln | Pro | Phe | Val | Lys | Tyr | Ala | Thr | Leu | Ile | Ser | Asn |
| | | | 980 | | | | | 985 | | | | | 990 | | |
| Ser | Lys | Pro | Ser | Glu | Thr | Gly | Glu | Glu | Gln | Gly | Leu | Ile | Asn | Ser | Ser |
| | | 995 | | | | | 1000 | | | | | 1005 | | | |
| Val | Thr | Lys | Cys | Phe | Ser | Ser | Lys | Asn | Ser | Pro | Leu | Lys | Asp | Ser | Phe |
| | 1010 | | | | | 1015 | | | | | 1020 | | | | |
| Ser | Asn | Ser | Ser | Trp | Glu | Ile | Glu | Ala | Gln | Ala | Phe | Phe | Ile | Leu | Ser |
| 1025 | | | | | 1030 | | | | | 1035 | | | | | 1040 |
| Asp | Gln | His | Pro | Asn | Ile | Ile | Ser | Pro | His | Leu | Thr | Phe | Ser | Glu | Gly |
| | | | | 1045 | | | | | 1050 | | | | | 1055 | |
| Leu | Asp | Glu | Leu | Leu | Lys | Leu | Glu | Gly | Asn | Phe | Pro | Glu | Glu | Asn | Asn |
| | | | 1060 | | | | | 1065 | | | | | 1070 | | |
| Asp | Lys | Lys | Ser | Ile | Tyr | Tyr | Leu | Gly | Val | Thr | Ser | Ile | Lys | Lys | Arg |
| | | 1075 | | | | | 1080 | | | | | 1085 | | | |
| Glu | Ser | Gly | Val | Leu | Leu | Thr | Asp | Lys | Ser | Arg | Val | Ser | Cys | Pro | Phe |
| | | 1090 | | | | | 1095 | | | | | 1100 | | | |
| Pro | Ala | Pro | Cys | Leu | Phe | Thr | Asp | Ile | Arg | Val | Leu | Gln | Asp | Ser | Cys |
| 1105 | | | | | 1110 | | | | | 1115 | | | | | 1120 |
| Ser | His | Phe | Val | Glu | Asn | Asn | Ile | Asn | Leu | Gly | Thr | Ser | Ser | Lys | Lys |
| | | | | 1125 | | | | | 1130 | | | | | 1135 | |
| Thr | Phe | Ala | Ser | Tyr | Met | Pro | Gln | Phe | Gln | Thr | Cys | Ser | Thr | Gln | Thr |
| | | | 1140 | | | | | 1145 | | | | | 1150 | | |
| His | Lys | Ile | Met | Glu | Asn | Lys | Met | Cys | Asp | Leu | Thr | Val | | | |
| | | | 1155 | | | | | 1160 | | | | | 1165 | | |

US 6,270,981 B1

METHODS OF SCREENING COMPETITORS OF OB-R BINDING TO SHP-2-SH2 PEPTIDES

This application is a continuation-in-part of copending U.S. application Ser. No. 60/049,108, filed Jun. 9, 1997, the contents of which is hereby incorporated by reference. Throughout this application various publications are referenced. The disclosures of these publications in their entireties are hereby incorporated by reference into this application.

BACKGROUND OF THE INVENTION

Leptin

Leptin, the product of the obese gene (1), is secreted by adipocytes, and functions as a peripheral signal to the brain that regulates food intake and energy metabolism. Leptin is thought to exert its action in the hypothalamus through its receptor, OB-R "the sequence of which is set forth in SEQ ID NO:1" (2). Rodents with mutations that prevent normal expression of either leptin or full-length OB-R are profoundly obese, diabetic, and have a reduced metabolic rate (3). However, human obesity does not appear to be associated with mutations in the genes encoding leptin or OB-R (4, 5). Although mice with a mutant obese gene can be returned to normal weight by administration of recombinant leptin (6–8), it seems unlikely that this approach will succeed in obese humans because their serum leptin levels are chronically elevated (9–11). Obese humans, therefore, appear to be "leptin resistant" (9, 12, 13) in that they do not generate a signal commensurate with their serum leptin levels, perhaps because of defective transport of leptin across the blood-brain barrier (14) or an inadequate OB-R response. Analysis of OB-R signaling pathways may reveal alternative therapeutic approaches of boosting OB-R responses to overcome leptin resistance and reverse obesity.

Leptin and OB-R are members of the four-helical bundle cytokine and receptor superfamilies respectively (2, 15). OB-R is most closely related to the gp130 signal transducing receptor that is activated by cytokines such as IL-6 (CNTF: ciliary neurotrophic factor; IL-6: Interleukin-6; Jak: Janus kinase; NT-3: neurotrophin-3; SH2: Src homology domain 2; STAT: Signal Transducer and Activator of Transcription; TOBR: Trk-C-OB-R chimeric receptor) and CNTF, whose signaling pathways have been intensively studied (16, 17).

Ligand binding induces either homodimerization of gp130, or heterodimerization of gp130 with related signal transducing receptors, leading to activation of the receptor-associated Jaks (18, 19). The Jaks then phosphorylate gp130 on cytoplasmic tyrosine residues, forming phosphotyrosine motifs that recruit specific SH2-containing signaling molecules such as STAT3, and the protein tyrosine phosphatase SHP-2 (previously known as PTP1D, SH-PTP2 or Syp) (20). Removal or mutation of the phosphotyrosine motifs in the receptor eliminates activation of the corresponding SH2 target molecule (20). Cytoplasmic deletions appear to affect OB-R in a similar manner: there are multiple isoforms of OB-R corresponding to alternatively spliced products with different cytoplasmic domains (2, 21–24), but only one isoform with several potential phosphotyrosine motifs, known as the long form or OB-Rb, appears capable of mediating leptin's weight controlling effects (21, 22, 25, 26). Obese diabetic mice have a mutation in OB-R that prevents expression of the long OB-R splice isoform, which renders them incapable of appropriately mediating leptin's actions (21, 22). The finding that only the long form of OB-R contains the sequence YXXQ (2), which is a motif that specifies STAT3 activation (20), raised the possibility that STAT3 is critical for mediating leptin responses. Recent results verify that STAT3 is activated both in cultured cells (25–27) and in vivo (28) by the long form of OB-R, and not by a truncated OB-R or the long form of OB-R with a mutant YXXQ motif (26, 29). Although leptin-induced activation of overexpressed STAT1 and STAT5b is also observed in transfected cells (25, 26), only activation of STAT3 has been detected in vivo upon stimulation of hypothalamic OB-R by administration of leptin (28). Thus it appears likely, but unproven, that transcriptional activation of target genes by STAT3 in the hypothalamus is a critical pathway that mediates leptin's regulation of food intake and energy metabolism.

Assay Systems

Ligand-receptor assays rely on the binding of ligands to receptors to determine the presence and/or concentration of ligands in a sample. Ligand-receptor assays can be described as either competitive or non-competitive. Non-competitive assays generally utilize receptors in substantial excess over the concentration of ligand to be determined in the assay. Sandwich assays, in which the ligand is detected by binding to two receptors, one receptor labeled to permit detection and a second receptor frequently bound to a solid phase to facilitate separation from unbound reagents, such as unbound labeled first receptor, are examples of non-competitive assays.

Competitive assays generally utilize ligand from the sample, a ligand analogue labeled to permit detection, and the competition of these species for a limited number of binding sites provided by the ligand receptor. Those skilled in the art will appreciate that many variations of this basic competitive situation have been previously described. Examples of ligands which are commonly measured by competitive ligand-receptor assays include haptens, hormones and proteins. Antibodies or receptorbodies that can bind these classes of ligands are frequently used in these assays as ligand receptors.

Competitive ligand-receptor assays can be further described as being either homogeneous or heterogeneous. In homogeneous assays, all of the reactants participating in the competition are mixed together and the quantity of ligand is determined by its effect on the extent of binding between ligand receptor and labeled ligand analogue. The signal observed is modulated by the extent of this binding and can be related to the amount of ligand in the sample. U.S. Pat. No. 3,817,837 describes such a homogeneous, competitive immunoassay in which the labeled ligand analogue is a ligand-enzyme conjugate and the ligand receptor is an antibody capable of binding to either the ligand or the ligand analogue. The binding of the antibody to the ligand-enzyme conjugate decreases the activity of the enzyme relative to the activity observed when the enzyme is in the unbound state. Due to competition between unbound ligand and ligand-enzyme conjugate for antibody binding sites, as the ligand concentration increases the amount of unbound ligand-enzyme conjugate increases and thereby increases the observed signal. The product of the enzyme reaction may then be measured using a spectrophotometer.

In general, homogeneous assay systems require both an instrument to read the result and calibration of the observed signal by separate tests with samples containing known concentrations of ligand. The development of homogeneous assays has dominated competitive assay research and has resulted in several commercially available systems.

Heterogeneous, competitive ligand-receptor assays require a separation of bound labeled ligand or receptor from the free labeled ligand or receptor and a measurement of either the bound or the free fraction. Methods for performing such assays are described in U.S. Pat. Nos. 3,654,090, 4,298,685, and 4,506,009. U.S. Pat. Nos. 4,125,372, 4,200,690, 4,246,339, 4,366,241, 4,446,232, 4,477,576, 4,496,654, 4,632,901, 4,727,019, and 4,740,468 describe devices and methods for ligand-receptor assays that develop colored responses for visual interpretation of the results.

In the case of a competitive immunoassay, a labelled ligand reagent is bound to a limited and known quantity of receptor reagent. After that reaction reaches equilibrium, the ligand to be detected is added to the mixture and competes with the labelled ligand for the limited number of receptor binding sites. The amount of labelled ligand reagent displaced, if any, in this second reaction indicates the quantity of the ligand to be detected present in the fluid sample.

Another approach, a non-competitive immunochromatographic assay, is described in U.S. Pat. Nos. 4,168,146 and 4,435,504. This assay provides a method for quantitatively determining the presence of a single analyte in a sample in a visually interpreted immunoassay. U.S. Pat. No. 5,089,391 describes a method for performing competitive ligand-receptor assays so as to be able to semiquantitatively or quantitatively determine the concentration of the ligand.

SUMMARY OF THE INVENTION

The present invention relates to a novel method of screening for agents that are capable of enhancing the weight reducing effect of leptin. The invention is based on applicants' discovery that SHP-2 can act as a negative regulator of certain cytokine receptors, and specifically blocking activation of SHP-2 by leptin could provide a possible mechanism to surmount leptin resistance in obese individuals.

The present invention further comprises use of agents discovered using the assay system described herein for the treatment of conditions such as obesity, that are caused, in part, by leptin resistance.

The invention further provides for agents that may be used to enhance the effect of therapeutic doses of leptin.

BRIEF DESCRIPTION OF THE DRAWINGS

FIG. 5. Timecourse of STAT3 tyrosine phosphorylation is unchanged in cells expressing OB-RY986F. COS cells expressing native OB-R or mutant OB-RY986F were either left unstimulated (0), or stimulated with leptin for 10 minutes, washed 1× in PBS, and either lysed immediately (10 minutes) or incubated in media (without leptin) for the indicated times and then lysed ("Time" equals total incubation interval from addition of leptin). Myc (A) and STAT3 (B and C) immunoprecipitates (IP) were immunoblotted (Blot) with antibodies to P-Tyr (A), P-STAT3 (B) and STAT3 (C). The phosphorylated form of each protein is indicated by a superscrited P on the right side of each panel.

μM peptide were incubated together. GST-SHP1-SH2 or GST-SHP2-SH2 was immunoprecipitated with Glutathione Sepharose (Pharmacia), and co-precipitating EPOR-cyto-P was visualized with an anti-Trx antibody.

Figure 11:
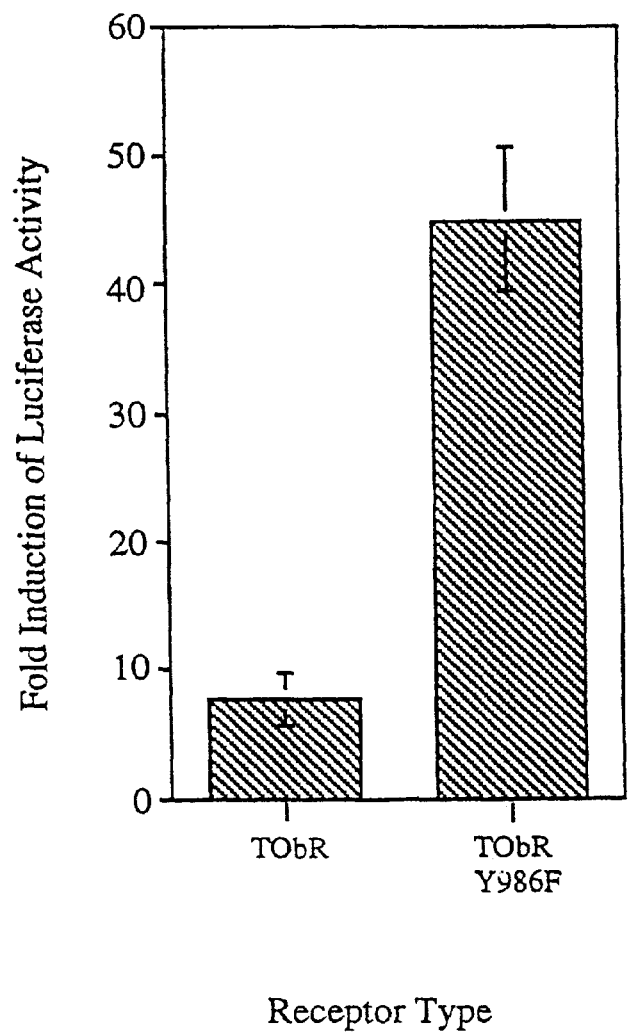

FIG. 11. Mutation of Y986 in OB-R leads to an enhancement of leptin-stimulated STAT3-mediated luciferase gene induction. Neuroblastoma (NBFL) cells were transiently transfected with the indicated TrkC—OB-R receptor constructs and 3(G3)-Cy6-LUC reporter. The mean fold induction of luciferase activity ± standard error (n=3) is indicated.

FIGS. 12A–12B. Amino acid sequence of OB-R.

DETAILED DESCRIPTION OF THE INVENTION

The present invention is based on applicants' discovery regarding certain signaling molecules in the signal transduction pathway activated upon the binding of leptin to its receptor OB-R. Applicants have discovered that the interaction of the OB-R cytoplasmic domain with the signaling molecule SHP-2 results in down-regulation of STAT-mediated gene induction, which in turn results in down regulation of the effect of leptin on weight reduction.

Accordingly, based on this discovery, Applicants have developed assay systems designed to identify agents that are capable of interfering with the interaction between the OB-R and the SHP-2 molecule, thereby preventing the down-regulation of the STAT3 signaling molecule. Agents identified using this assay system should enhance the weight reducing effect of leptin.

According to the invention, a set of reagents which were used to directly demonstrate that the SH2 domains of SHP-2 directly interacts with the region encompassing tyrosine-phosphorylated Y986, provide a means to screen for potential therapeutic agents that block this interaction.

In one embodiment, these reagents are created as follows: the tandem SH2 domains of SHP-2 are produced in bacteria as a fusion to GST, which are expressed and purified by standard methods. Two distinct phosphotyrosine containing reagents are used as targets of SHP-2 binding. The first is a synthetic phosphopeptide encompassing Y986 containing a C-terminal FLAG epitope. The second reagent, is a GST fusion protein containing the entire cytoplasmic domain of human OB-R, which was phosphorylated on tyrosine residues in E. coli by secondarily inducing the ectopic expression of a mammalian tyrosine kinase following the primary induction of expression of the GST-fused OB-R cytodomain.

As demonstrated in Example 1, both phosphotyrosine-containing reagents show specific binding to the SH2 domains of SHP-2. Specificity is demonstrated by the fact that other phosphopeptides do not bind to GST-SHP2-SH2, and a tyrosine-phosphorylated OB-R cytoplasmic domain construct containing the Y986F mutation no longer binds to GST-SHP2-SH2.

The present invention also contemplates the use of the entire cytoplasmic domains of cytokine receptors for screening purposes, wherein an assay system is being utilized in which the aim is to measure the interaction between the cytoplasmic domain and downstream signaling molecules such as SHP-1 and SHP-2. Unexpectedly, tyrosine-phosphorylated GST-OBR apparently binds with much higher affinity to GST-SHP2-SH2 reagent, as indicated by the inability of a large excess of the phosphopeptide to block binding, than does the phosphopeptide. One possible explanation of this result is that the simple phosphopeptide is "floppy" in that it can undertake many different conformations, of which only a limited subset can effectively bind to the SH2 domains. In contrast, the corresponding region imbedded in the context of the tyrosine-phosphorylated cytoplasmic domain may be constrained to a particular conformation that is in the proper orientation to bind the SH2 domain, which thus results in a higher observed energy of interaction. A similar result was observed for the interaction of the SH2 domains of SHP-1 with its target phosphotyrosine sequence in the cytoplasmic domain of the erythropoietin receptor (EPOR). Very poor binding was observed for GST-SHP1-SH2 binding to a synthetic phosphopeptide from EPOR, while the tyrosine-phosphorylated cytoplasmic domain bound well. These examples provide evidence supporting the existence of a previously unknown general principle that utilization of larger cytoplasmic domains containing tyrosine-phosphorylated target sequences that bind SH2 domains may provide superior reagents for screening for therapeutic agents to block that interaction.

In addition, the use of the entire cytoplasmic domain of the cytokine receptor provides an additional advantage. Both of the tyrosine phosphatases SHP-1 and SHP-2 are involved in the downstream signaling pathways of a wide variety of receptors. In preferred embodiments, agents are discovered that bind to the cytokine receptor cytoplasmic domains to block interaction of the SHP molecule with their tyrosine-phosphorylated targets, giving greater specificity than therapeutic agents that block by binding to the phosphatase. Accordingly, the present invention further provides for use of tyrosine-phosphorylated cytoplasmic domains to provide a much higher likelihood of obtaining therapeutic agents that block by binding to the cytoplasmic domain, since they present a more precise mimic and larger molecular surface for interaction than does a simple unstructured phosphopeptide.

According to the invention, assay systems are utilized which are designed to measure the interaction between the SH2 binding domain of the cytokine receptor and the phosphatase comprising the SH2 domain. In a preferred embodiment, the SH2 binding domain of the cytokine receptor, which must contain a phosphorylated tyrosine residue, is presented in the assay as the full cytoplasmic domain, which, as described above, appears to present the binding domain in an appropriate conformation and which provides a larger surface area in which a competing agent might interact.

The present invention therefore involves a method of screening for a molecule capable of competing with OB-R for binding to SHP2-SH2 comprising:
  a) contacting a phosphopeptide comprising the Y986 domain of OB-R under conditions in which the Y986-containing phosphopeptide is capable of binding to a peptide comprising the SH2 domain of SHP2;
  b) determining the amount of the Y986-containing domain that binds to the SHP2-SH2 containing peptide;
  c) contacting a known amount of the Y986 containing phosphopeptide to the SHP2-SH2 containing peptide, in the presence of a sample suspected of containing the molecule capable of competing with the Y986 containing phosphopeptide, under the same conditions used in b);
  d) determining the amount of the Y986-containing phosphopeptide that binds to the SHP2-SH2 containing peptide;
  e) comparing the amount from (b) with the amount from (d), wherein a lesser amount in (d) indicates the presence of a molecule capable of competing with the Y986 containing phosphopeptide for binding to the SHP2-SH2 domain.

As used herein, the phosphopeptide comprising the Y986 comprising domain is any peptide or protein that is derived from OB-R and which comprises the Y986 site of the protein. Accordingly, this domain may be either a phosphopeptide or the entire cytoplasmic domain of OB-R. In a preferred embodiment, the Y986 phosphopeptide is the entire cytoplasmic domain, which, as described above, may have enhanced properties which make it more useful in screening systems.

In alternative embodiments, the phosphopeptide is derived from the SH2 binding site derived from the cytoplasmic domains of other cytokine receptors, such as EPOR, for which SH2 phosphatases are negative regulators of receptor signaling. For example, SHP-1 has been shown to suppress signaling from the IL-3 receptor (35). Accordingly, the present invention contemplates an assay system using the SHP-1-SH2 domain and a phophopeptide comprising the SH2 binding domain of the IL-3 receptor.

Thus, assay systems are developed in which the interaction between the SH2 binding domain of a ctyokine receptor and the SH2 domain of an SH2 phosphatase that acts as a negative regulator in signaling may be measured, and agents identified with interfere with this interaction. Such assay systems would contain
  a) a peptide comprising an SH2 domain of an SH2 phosphatase;
  b) a phosphopeptide comprising the tyrosine phosphorylated SH2 binding domain of a cytokine receptor; and
  c) a means for detecting the interaction between said SH2 domain and said SH2 binding domain.

The present invention also provides for assay systems that may be used according to the methods described supra. Such assay systems may comprise in vitro preparations of the Y986 containing phosphopeptide and or SH2 continuing peptide, e.g. affixed to a solid support, or may, preferably, comprise cells that express one or both of these peptides.

The present invention further comprises uses of agents identified using the assay systems described herein to enhance the therapeutic effect of endogenous leptin, as well as exogenously supplied leptin or leptin derivatives or chimeras or ligandbodies in accordance, for example, with published applications WO97/11192 (published Mar. 12, 1997; WO97/02004 (published Jan. 23, 1997); WO97/06816 (published Feb. 27, 1997); and WO97/00319 (published Jan. 3, 1997).

EXAMPLES

Example 1
Demonstration that SHP-2 Interaction with OB-R Downregulates Leptin Effect
Materials and Methods
Expression Constructs and Cell Transfection.

The cytoplasmic domain and full-length human OB-R was cloned by PCR using human fetal liver and adipocyte cDNA (Clontech) and cloned into the expression vectors pCMX and pMT21. Chimeric receptors were constructed by fusing the extracellular domain and transmembrane domain of TrkC (amino acids 1 to 458) to the cytoplasmic domain of OB-R (amino acids 865–1165). A triple myc epitope tag was added at the C-terminus of all OB-R constructs (18). Truncation and point mutant constructs were generated by PCR and the sequences of all constructs were verified. Expression constructs were transfected into COS-7 cells using lipofectamine (GIBCO-BRL); 36–48 hours after transfection, cells were starved for either 2 hours for chimeric receptors or overnight for full-length receptors prior to stimulation.

Immunoprecipitation and Western Blotting.

Cells were stimulated with 50 ng/ml of human NT-3 for 15 min or 100 ng/ml of human leptin (R&D Systems) for 10 min. Cells were then lysed in a 1% Brij 96 buffer and receptor was immunoprecipitated with anti-myc antibody 9E10 (18) followed by protein G-sepharose (Pharmacia). Unbound lysate was then immunoprecipitated with anti-P-Tyr antibody (UBI, Lake Placid) or agarose-conjugated anti-SHP-2 antibody (Santa Cruz Biotechnology). For analysis of the STAT3 tyrosine phosphorylation state, STAT3 was first immunoprecipitated with anti-STAT3 antibody (Transduction Labs), and the unbound lysate was then immunoprecipitated with anti-myc antibody. Immunoprecipitated proteins were separated on SDS-PAGE and proteins were immunoblotted with antibodies to SHP-2, STAT3, Jak1 (all from Transduction Laboratories), Jak2, P-Tyr (UBI), or myc and visualized by chemiluminescence (DuPont NEN). Endogenous STAT3, SHP-2, Jak1 and Jak2 is being detected in all immunoblotting experiments.

Luciferase Reporter Gene Assay.

Expression constructs (1 $\mu$g) for OB-R, OB-RY1141F, OB-RY986F, OB-RY1078, 1079F, and OB-RY986, 1141F were co-transfected with 1 $\mu$g of 3(G3)-Cy6-LUC and 0.1 $\mu$g of pCMX.LacZ into COS-7 cells (6-well dishes) using lipofectamine. The day after transfection, media was changed to serum-free OptiMEM (GIBCO-BRL) and then treated with 100 ng/ml murine leptin (PeproTech) or human leptin (R&D Systems) for 24 hours. Expression constructs for TOBR and TOBRY986F were co-transfected with 3(G3)-Cy6-LUC and pCMX.LacZ into neuroblastoma (NBFL) cells by calcium-phosphate precipitation for 6 hours. Cells were subsequently treated with neurotrophin-3 (NT-3) at 20 ng/ml for 36 hours. Luciferase and $\beta$-galactosidase activities were measured in cell lysates (30) and luciferase activity was normalized to $\beta$-galactosidase activity to control for transfection differences.

Results

Figure 1:
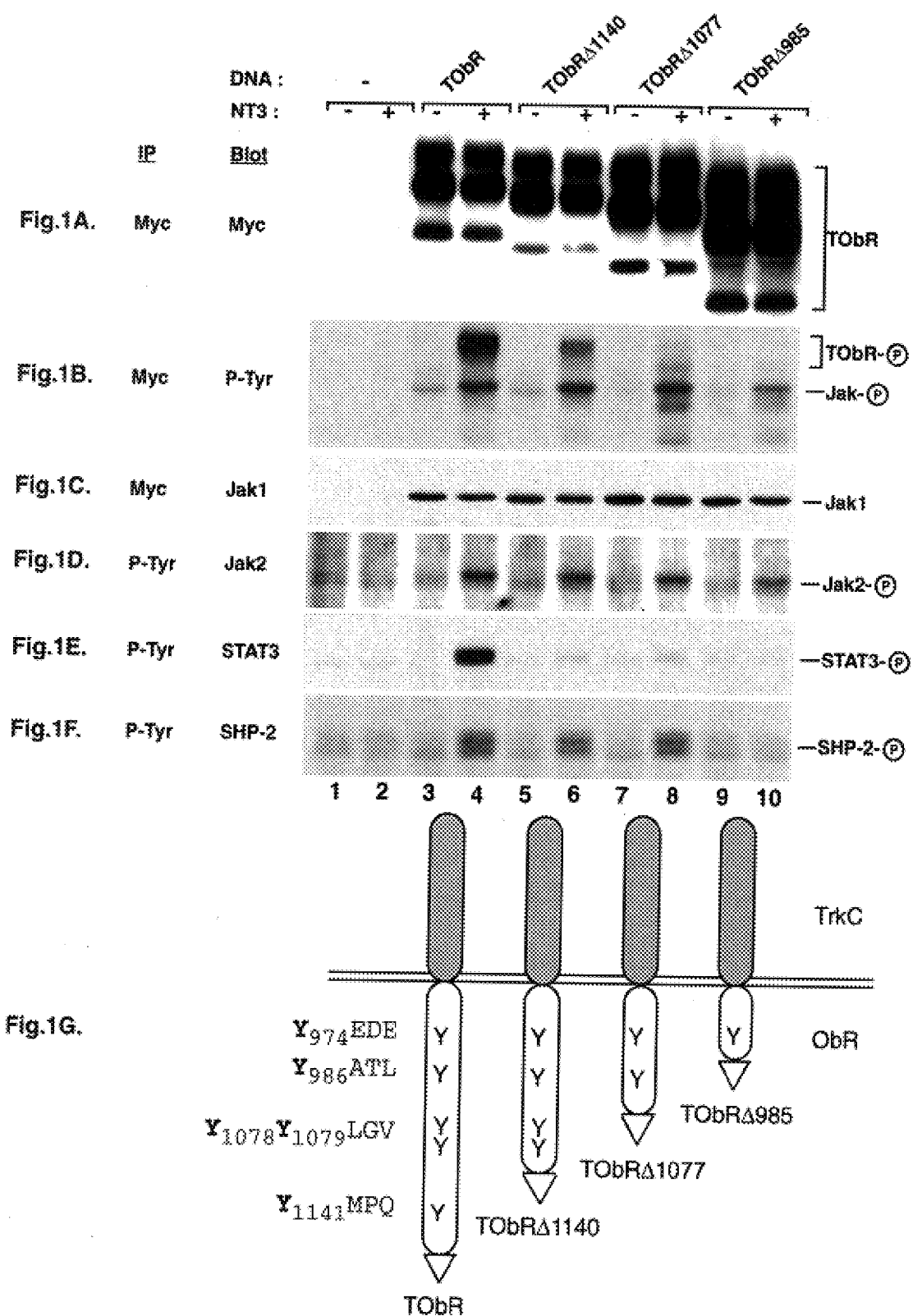
FIG. 1. NT-3 stimulation of TrkC-OB-R chimeras leads to phosphorylation of receptor, Jaks, STAT3, and SHP-2. Immunoblots (Blot) of myc and P-Tyr immunoprecipitates (IP) from unstimulated (−) and stimulated (+) cells transfected with TrkC-OB-R constructs. Truncation constructs are designated by the number of the last amino acid of the OB-R cytoplasmic domain present before the myc epitope tag (indicated by a triangle), and the amino acids surrounding each tyrosine are also indicated (bottom). The phosphorylated form of each protein is indicated by a superscripted P on the right side of each panel.

We first examined OB-R signaling by creating a series of epitope-tagged chimeric receptors consisting of the extracellular and transmembrane domains of the receptor tyrosine kinase TrkC fused to the cytoplasmic domain of the long form of human OB-R, thus allowing the use of a surrogate ligand to specifically activate the OB-R signaling pathway. Analogous chimeric receptors were used previously to investigate gp130 signaling, and showed activation of the identical pathways as native gp130 (20). Following transient transfection of COS cells with a vector expressing the TrkC—OB-R chimera (TOBR), receptor dimerization with NT-3 resulted in ligand-dependent tyrosine phosphorylation of TOBR and downstream signaling molecules (FIG. 1). As first observed for gp130 (18), and subsequently noted for many other cytokine receptors, preassociation of Jak1 with the OB-R cytoplasmic domain was observed in the absence of ligand (FIG. 1C), and receptor activation resulted in tyrosine phosphorylation of the associated Jak1 (FIG. 1B). The receptor-associated Jak is most likely Jak1 as immunoblots of myc immunoprecipitates show co-migration of Jak1, but not Jak2, with the tyrosine phosphorylated Jak (FIGS. 1B and C, lane 4 and data not shown). Jak2 also becomes tyrosine phosphorylated upon receptor activation (FIG. 1D), but is not found associated with OB-R following detergent lysis of the cells. Direct immunoprecipitation of Jak1 followed by immunoblotting with anti-phosphotyrosine revealed that Jak1 becomes tyrosine phosphorylated upon NT-3 stimulation. In addition, receptor was found to co-immunoprecipitate with Jak1 independent of ligand stimulation. Ligand-dependent tyrosine phosphorylation of STAT3 was observed (FIG. 1E, lane 4), consistent with previous observations that STAT3 is activated by OB-R (25–28). We also found that activation of OB-R mediates tyrosine phosphorylation of the protein tyrosine phosphatase SHP-2 (FIG. 1F, lane 4), which has not been previously reported to be a target of leptin action.

To identify regions of the OB-R that are required to direct phosphorylation of downstream signaling molecules, we created a series of chimeras containing C-terminal truncations of TOBR that successively eliminate tyrosine residues from the receptor cytoplasmic domain (FIG. 1). For gp130 and other cytokine receptors, phosphorylated tyrosines along with their surrounding amino acids constitute modular tyrosine-based motifs that recruit specific downstream targets through interaction with their SH2 domains (20, 31). Stimulation-dependent STAT3 phosphorylation is not observed for the construct TOBRΔ1140, in which the sequence YMPQ, a tyrosine-based motif capable of specifying STAT3 activation (20), has been deleted (FIG. 1E, lane 6). Tyrosine phosphorylation of the receptor, Jak and SHP-2 are still observed for TOBRΔ1140 (FIGS. 1B, D, F; lane 6); however, receptor phosphorylation is dramatically reduced. Deletion of the tandem tyrosine residues at 1078 and 1079 has no effect on phosphorylation of the Jaks or SHP-2 (FIGS. 1B, D, F; lane 8). In contrast, cells expressing the construct TOBRΔ985 cannot mediate SHP-2 phosphorylation (FIG. 1F, lane 10), although this truncated receptor can still confer phosphorylation of Jak2 and receptor-bound Jak1 (FIGS. 1B, D; lane 10). TOBRΔ985 lacks the sequence YATL, which is similar to other tyrosine-based motifs that interact with the SH2 domains of SHP-2 (32, 33), and may specify SHP-2 interaction with OB-R.

To confirm our assertion that the specific tyrosine residues within OB-R are critical for specifying STAT3 and SHP-2 phosphorylation, we created epitope-tagged versions of OB-R containing mutations that substitute phenylalanine for tyrosine within the YMPQ or YATL motifs, and examined their ability to activate STAT3 and SHP-2. Leptin stimulation of COS cells expressing OB-R results in phosphorylation of the receptor, STAT3 and SHP-2 (FIGS. 2B, C, D; lane 3), which corroborates the observations made with the chimeric receptors, and confirms that leptin indeed induces tyrosine phosphorylation of wildtype OB-R in COS cells. Mutation of the tyrosine within the YMPQ motif in OB-R$_{Y1141F}$ not only eliminates STAT3 activation upon leptin stimulation as previously reported (26), but also markedly reduces the level of receptor phosphorylation (FIGS. 2B, C; lane 5). Nonetheless, phosphorylation of SHP-2 is still observed (FIG. 2D; lane 5). However, mutation of the YATL motif in OB-R$_{Y986F}$ eliminates leptin-stimulated SHP-2 phosphorylation (FIG. 2D; lane 7), but does not affect STAT3 phosphorylation (FIG. 2C; lane 7). In contrast, mutation of the tyrosine within the YMPQ motif in OB-RY1141F results in SHP-2 phosphorylation upon leptin stimulation (FIG. 2D; lane 5), however, as expected, STAT3 phosphorylation is no longer observed (FIG. 2C, lane 5). Stimulation of OB-R possessing phenylalanine substitutions at Y1078,1079 results in phosphorylation of both STAT3 and SHP-2, while OR-R carrying a double mutation, OB-RY986,1141F cannot direct phosphorylation of either STAT3 or SHP-2 (data not shown). This result demonstrates that Y986 within OB-R is required to specifically mediate the phosphorylation of SHP-2. We have also observed direct binding of recombinant SH2 domains derived from SHP-2 with a synthetic peptide corresponding to the phosphorylated YATL sequence from.

Figure 2:
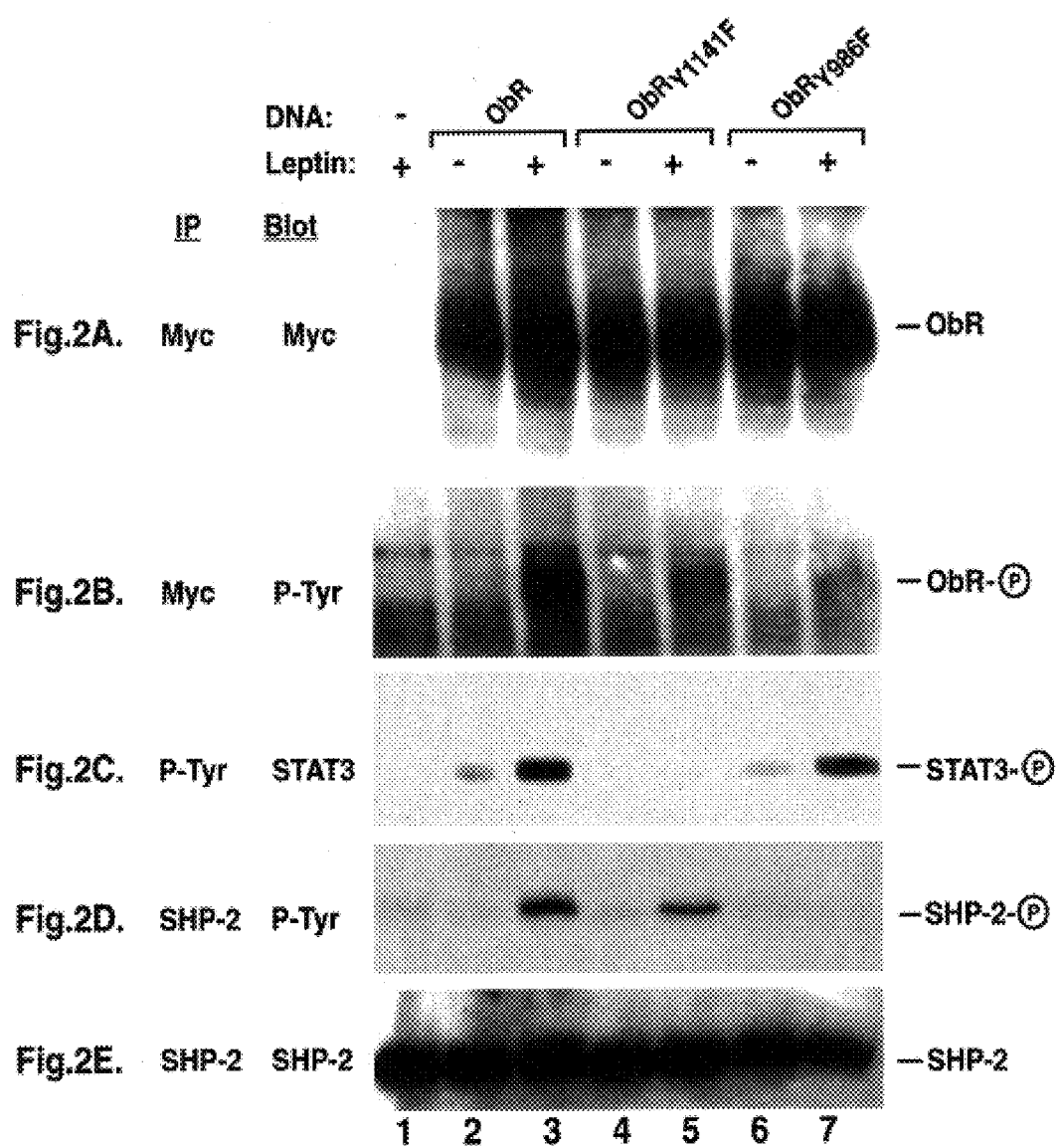
FIG. 2. SHP-2 phosphorylation is dependent on tyrosine 986. Immunoblots (Blot) of myc, P-Tyr or SHP-2 immunoprecipitates (IP) from unstimulated (−) and leptin stimulated (+) cells transfected with the full-length OB-R constructs. Phenylalanine (F) substitutions were made at the indicated tyrosines (Y).
Figure 3:
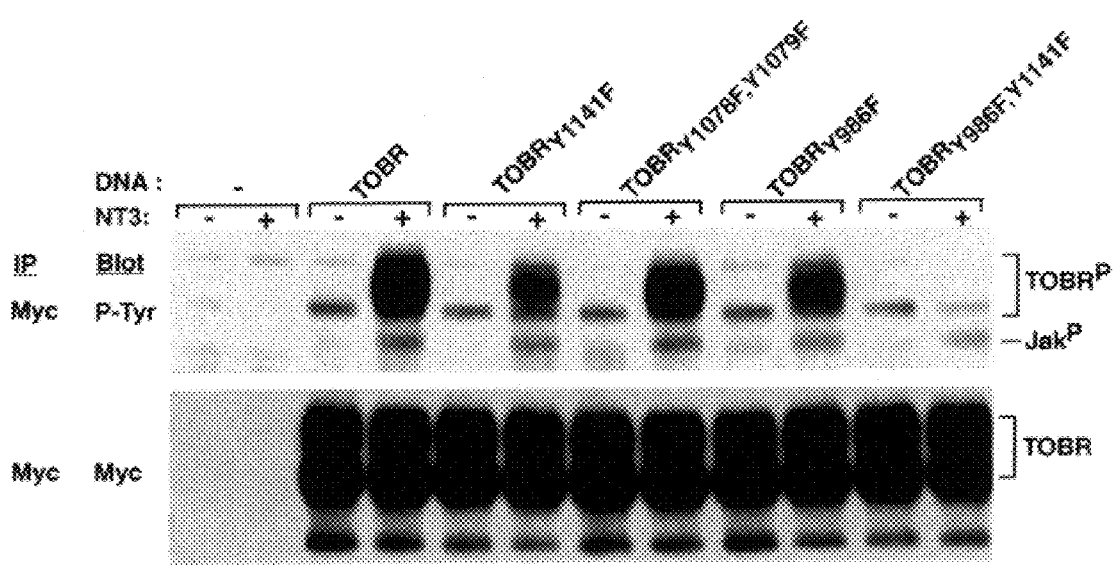
FIG. 3. Majority of stimulation-dependent phosphorylation occurs on tyrosines 986 and 1141. Immunoblots (Blot) of immunoprecipitated proteins (IP) from unstimulated (−) and NT-3 stimulated (+) cells transfected with TrkC-OB-R constructs.

Mutant OB-R with phenylalanine substitution at either residue Y1141 or Y986 resulted in decreased receptor phosphorylation after leptin addition despite undiminished levels of receptor expression and phosphorylation of SHP-2 or STAT3 respectively (FIG. 2). One interpretation of this result is that residues 1141 and 986 are the only major sites of tyrosine phosphorylation in OB-R in COS cells, so that mutation of either leads to a 50% decrease in the observed signal. To assess this possibility, we analyzed the level of tyrosine phosphorylation of various phenylalanine substitution mutants of the chimeric receptor TOBR, which is expressed at higher levels than OB-R and gives a more robust tyrosine phosphorylation response (FIG. 1 vs. FIG. 2). Consistent with the above hypothesis, point mutants simultaneously eliminating tyrosines 1078 and 1079 produced a receptor with levels of tyrosine phosphorylation comparable to parental TOBR, while mutation of either tyrosine at position 1141 or 986 gave a substantial, but similar abrogation of tyrosine phosphorylation relative to TOBR (FIG. 3). Moreover, a double mutant substituting phenylalanine at positions 1141 and 986 showed no detectable receptor tyrosine phosphorylation upon activation, but displayed undiminished levels of Jak phosphorylation (FIG. 3). These results indicate that tyrosine 986 and 1141 are the major sites of tyrosine phosphorylation upon ligand stimulation of OB-R in COS cells.

The role that SHP-2 and its relative SHP-1 (previously known as PTP1C, SH-PTP1 or HCP) play in signaling has been examined for several receptors. SHP-1 generally functions as a negative regulator of receptor signaling in hematopoietic cells where it is expressed. Recruitment of SHP-1 to the activated erythropoietin receptor causes inactivation of receptor-bound Jak2 and dampens proliferation (34). SHP-1 has been shown to similarly suppress signaling from the IL-3 receptor (35) and the FcγRIIB1 receptor (36). The absence of SHP-1 in mutant motheaten mice leads to dramatic increases in the total number of myeloid precursor cells of multiple lineages resulting from loss of the suppressive function of SHP-1 (37). In contrast, the ubiquitously expressed SHP-2 generally acts to positively regulate signaling, as found for the prolactin (38), PDGF (39, 40), insulin (41), interferon (42), and EGF (39, 40) receptor systems. For the PDGF receptor, tyrosine phosphorylated SHP-2 acts as an adaptor molecule that recruits GRB2 and Sos, members of the signaling pathway leading to activation of Ras and the MAP kinase ERK (40). Likewise, gp130 apparently uses SHP-2 to activate ERK2 by coupling to Grb2 and Sos, leading to stimulation of mitogenesis in BAF cells (43). SHP-2 is not exclusively a positive regulator of signaling as it associates with CTLA and functions to downregulate T cell receptor signaling (44).

Figure 4A:
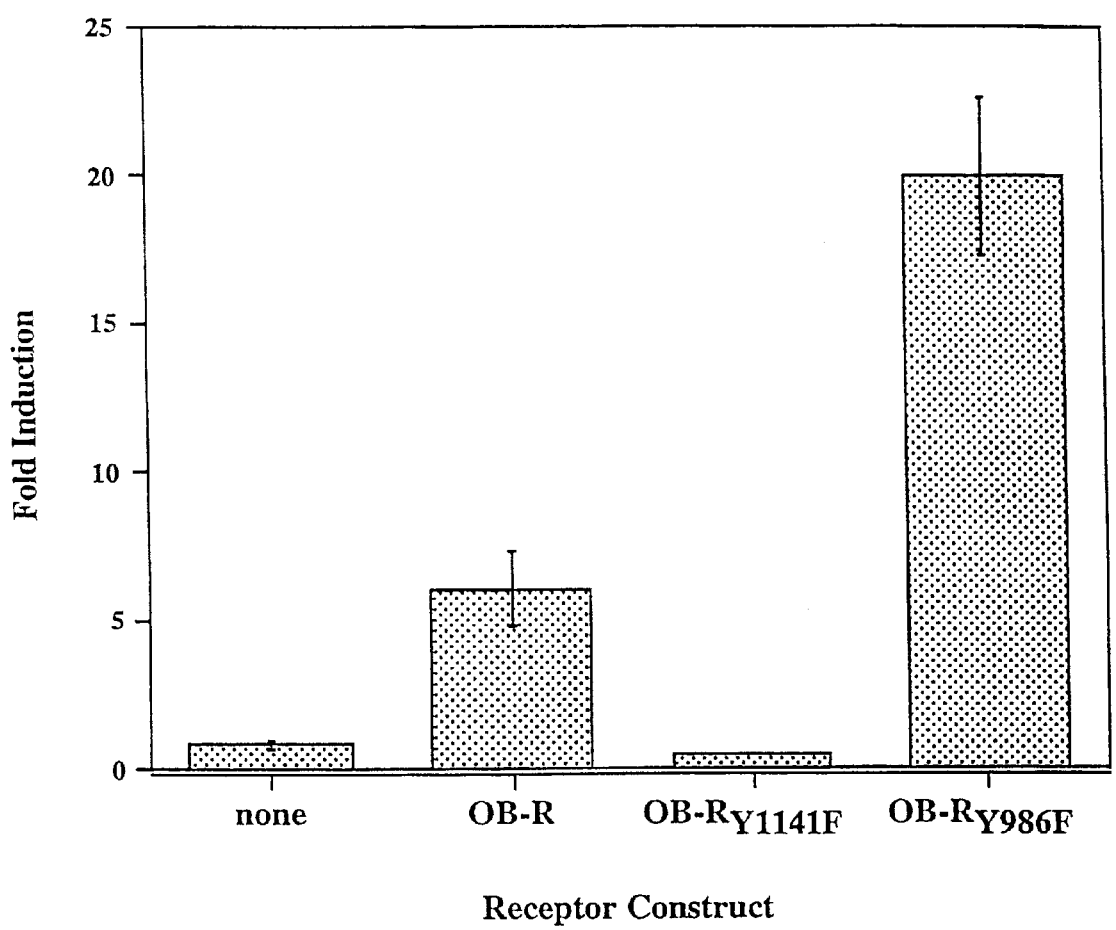
FIG. 4A. Mutation of Y986 in OB-R leads to an enhancement of leptin-stimulated luciferase activity. The fold induction of stimulated compared to non-stimulated cells is indicated as the mean ± standard error.
Figure 4B:
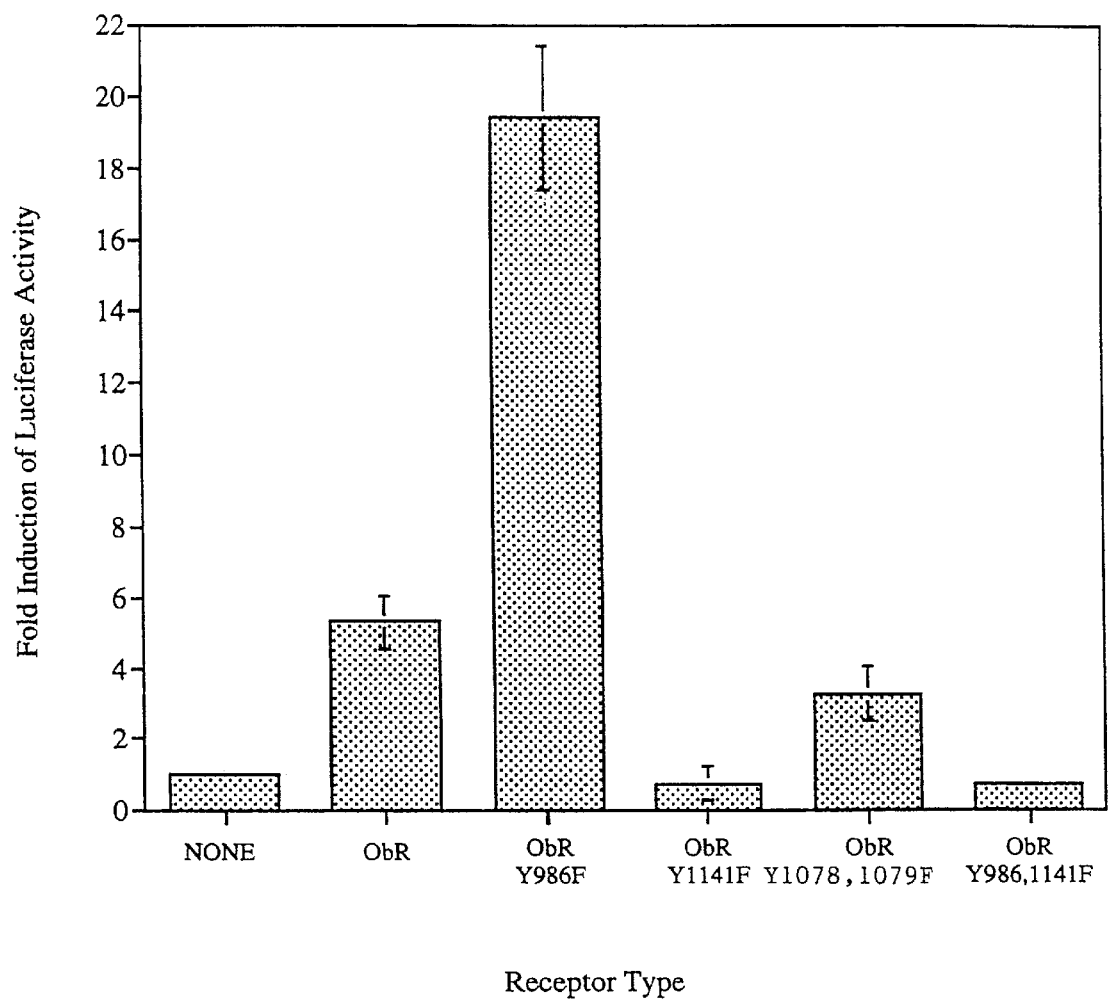
FIG. 4B. Mutation of Y1078 and Y1079 (double mutation) in OB-R leads to induction of similar luciferase levels as the native receptor. The fold induction of stimulated compared to non-stimulated cells is indicated as the mean ± standard error.

To assess the role of SHP-2 in regulating leptin-stimulated gene induction, we co-transfected COS cells with constructs encoding OB-R and the luciferase reporter 3(G3)-Cy6-LUC, which contains 3 copies of a STAT3 responsive DNA element from the promoter that drives expression of the neuropeptide VIP (30). A 6-fold induction of luciferase activity was observed upon leptin stimulation of cells expressing wild type OB-R (FIG. 4A). There was no induction of luciferase activity upon stimulation of cells expressing the mutant construct OB-RY1141F, in which the mutated tyrosine motif is no longer competent to allow activation of STAT3 (FIG. 4A), while activation of the double mutant OB-RY1078,1079F induced similar luciferase levels as the native receptor (FIG. 4B). Surprisingly, leptin stimulation of cells expressing the mutant receptor OB-RY986F, which can mediate phosphorylation of STAT3 but not SHP-2, results in a 20-fold increase in luciferase activity (FIG. 4A). Thus SHP-2, in contrast to its role in most other receptor systems, is a negative regulator of STAT3-mediated gene induction following OB-R activation. An analogous finding is observed for gp130, where phenylalanine substitution of Y759, which prevents phosphorylation of SHP-2 upon activation of gp130, also gives rise to a much greater level of gene induction by STAT3 (51). Moreover, overexpression of the N-terminal SH2 domain of SHP-2, which acts as dominant negative regulator that binds to phosphorylated gp130 and blocks native SHP-2 phosphorylation, can enhance the CNTF-mediated upregulation of neuropeptides during cholinergic differentiation of sympathetic neurons (52). Thus SHP-2 plays a dual regulatory role for gp130, and possibly for OB-R, in that it is required to mediate activation of ERK (and mitogenesis in a BAF cell), but functions as a negative regulator to suppress STAT3-mediated gene induction.

The mechanism by which SHP-2 acts to downregulate STAT3-mediated signaling is unclear but may differ from that observed for SHP-1. Overall levels of tyrosine phosphorylation of STAT3 and receptor-associated Jak appear equal (FIG. 5) in native and mutant OB-RY986F which cannot recruit and activate SHP-2. In addition, there was also no difference in the duration of tyrosine phosphorylation of the receptor, STAT3, or receptor-associated Jak between native and mutant OB-RY986F (FIG. 5). Therefore, in contrast to the role of SHP-1 in EPOR signaling, SHP-2 may signal through a downstream effector, perhaps lying in the pathway leading to ERK activation, that can influence STAT3-mediated gene transcription. Alternatively, it is also possible that SHP-2 signaling involves the cytokine-inducible inhibitors of STAT signaling (46–48) to regulate levels of transcription upon ligand stimulation.

Activation of OB-R and gp130 result in the recruitment and activation of common signaling molecules, most notably STAT3 (25, 26, 28) and SHP-2. Thus, for both receptor systems STAT3 appears to be critical for mediating the individual ligand's biological actions. The receptor for CNTF, a neurocytokine, consists of the signal transducing components gp130 and LIFRβ, along with a specificity determining component CNTFRα. Interestingly, functional CNTF receptors are found in the hypothalamus, and administration of CNTF to humans mimics leptin's ability to reduce food intake and cause weight loss (49). Activation of CNTFR by systemic administration of CNTF to obese mice that lack either functional leptin (ob/ob) or OB-R (db/db) results in the reversal of their obesity phenotypes, including reduction of adiposity and hyperphagia (50). Both CNTF and leptin were shown to similarly activate STAT3 in a neuronal cell line and moreover, mediate the induction of the STAT3 responsive tis-11 gene in the hypothalamus of ob/ob mice (50). The potent and similar effects of CNTF and leptin on the reduction of food intake and the increase in energy expenditure in mutant obese mice are most likely due to common signaling pathways, ie. STAT3 activation, in the brain. Indeed, only STAT3 was activated upon leptin stimulation of hypothalamic ObR in vivo (28). It remains to be established whether the downregulation of STAT-mediated signaling occurs through a downstream effector, perhaps lying in the pathway leading to ERK activation, or whether SHP-2 phosphatase activity is directly involved in STAT deactivation.

An exciting, but speculative, implication of this finding is that specifically blocking the interaction of SHP-2 with OB-R may enhance leptin's STAT3-mediated effects, and possibly overcome leptin resistance by increasing the effectiveness of the endogenous leptin signal. Enhancing leptin-induced gene responses could possibly overcome leptin resistance by increasing the effectiveness of the endogenous leptin signal, thereby boosting leptin's weight-reducing effects in obese individuals. This possibility is analogous to one existing naturally for another cytokine: humans that express a truncated mutant of the erythropoietin receptor, which eliminates the tyrosine-based motif that recruits SHP-1, display enhanced erythropoietin action and increased levels of red blood cells that result from the failure to down-regulate the activated receptor (45).

Example 2

Assay System for Measuring the Binding of OB-R Cytoplasmic Domain to SHP2-SH2.

Materials and Methods

The GST-SHP2-SH2 construct consists of the two SH2 domains of SHP2 fused downstream of glutathione-S-transferase (GST) from *Schistosoma japonicum*. The fusion has aa 2–224 of SHP2 cloned as an EcoRI/BamHI fragment into pGEX-3X and was expressed in *E. coli*. The SHP2-SH2-Fc construct consists of the same amino acids as the above fusion fused to human IgG-Fc as a BlpI/SrfI fragment in pMT21 and was expressed in COS-7 cells.

The GST-SHP1-SH2 construct consists of the two SH2 domains of SHP1 fused downstream of GST. Amino acids 2–221 of SHP1 were cloned as a EcoRI/BglII fragment into pGEX-3X and expressed in *E. coli*.

The SHP1-SH2-Fc construct consists of the same amino acids as the above fusion fused to human IgG-Fc as a BlpI/SrfI fragment in pMT21 and expressed in COS-7 cells.

The OB-R phosphopeptide came from Research Genetics and has the sequence QPFVKp-YATLISNDYKDDDDK. The last eight amino acids are a flag tag.

The EPOR phosphopeptide came from Research Genetics and has the sequence CPHLKp-YLYLVVSDDYKDDDDK. The last eight amino acids are a flag tag.

The OB-R cytoplasmic domain was expressed in *E. coli* as a fusion with GST. The fusion was to amino acids 865–1165 and contains the full cytoplasmic region. It was cloned as a SalI/NotI fragment from pCMX-Tob (10) into pGEX-5X-1. Both triple myc tagged and triple flag tag versions were made (fusion to COOH end of OB-R). THE EPOR cytoplasmic domain was expressed in *E. coli* as a fusion with *E. coli* thioredoxin (Trx) and as fusion to GST. The latter was tagged with a triple flag tag. EPOR-cyto was cloned as a BglII/NotI fragment from pMT21-huEPOR, including amino acids 258–485 of the mature protein into pGEX-5X-1 and pET32(a).

To get phosphorylated protein the receptor cytoplasmic domain clones were expressed in an *E. coli* that carried another plasmid encoding ELK Stratagene, La Jolla, Calif.). The gene for this kinase is under the control of the trp promoter and is induced by Trp starvation. The cytoplasmic domain fusions to GST are under the control of the IPTG inducible tac promoter, and the EPOR-cyto fusion to Trx is under the control of T7 polymerase. To get phosphorylated protein, the tac promoter or the T7 promoter is induced and cytoplasmic domain fusions are expressed for two hours. The cells are then centrifuged and resuspended in minimal medium plus a Trp competitor, indoleacrylic acid, inducing the synthesis of ELK and the subsequent phosphorylation of cytoplasmic domains.

Bindings were done as immunoprecipitations. Binding concentrations were typically 200 nM GST-SHP2-SH2 or GST-SHP1-SH2 and 15 nM phosphopeptide or cytoplasmic domain fusion in TBST (20 mM Tris, 150 mM NaCl, 0.1% Tween 20, pH 7.4) at 4° C. overnight. After binding either anti-flag mAb, M2, was added (for the phosphopeptide and flag tagged GST-OB-R-cyto) or anti-myc mAb, 9E10, was added (for the myc tagged GST-OB-R-cyto) and the proteins were precipitated with protein G-sepharose. Proteins were then detected on western blots using anti-GST polyclonal antibodies. For the EPOR-cyto-Trx fusion, the protein complexes were precipitated with glutathione-sepharose and the EPOR-cyto-Trx fusion was detected with anti-Trx polyclonal antibodies.

Results

Figure 6:
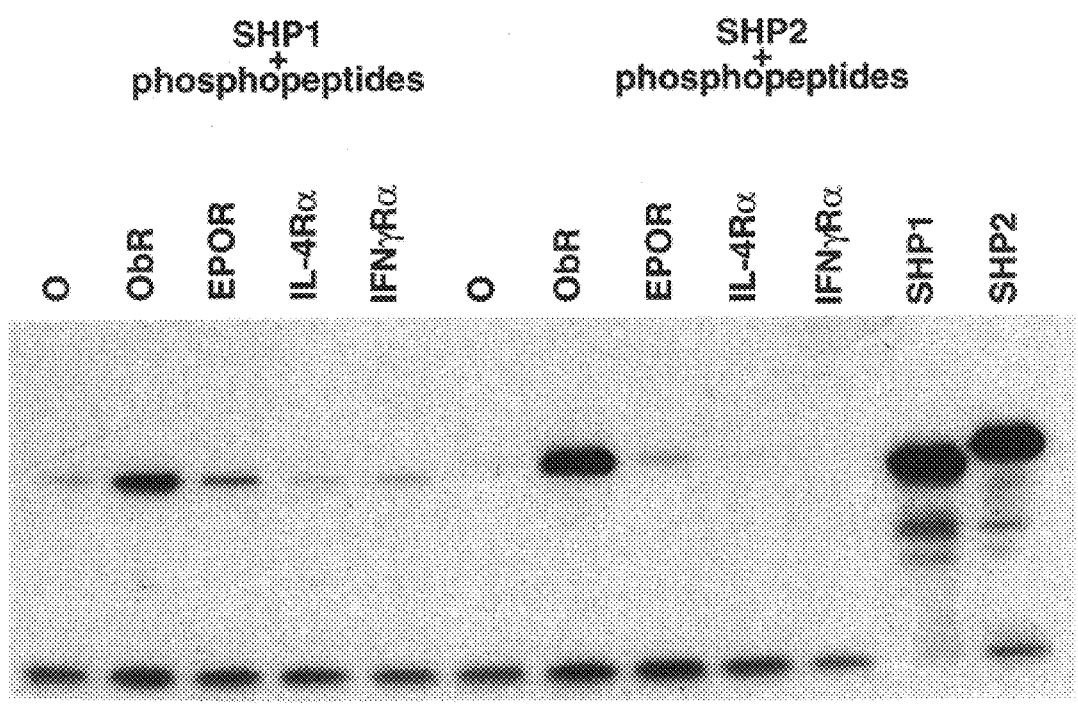
FIG. 6. SHP-2 specifically binds OB-R and this binding is dependent on Y986. (A). GST-SHP1-SH2 or GST-SHP2-SH2 were incubated with either no phosphopeptide, a phosphopeptide containing the sequence surrounding Y986 in OB-R, a phosphopeptide derived from the sequence surrounding Y401 of the cytoplasmic domain of the EPO receptor, a phosphopeptide derived from the sequence surrounding Y583 of the cytoplasmic domain of the IL-4 receptor a, or a phosphopeptide derived from the sequence surrounding Y440 of the cytoplasmic domain of the IFNγ receptor. Phosphopeptide was immunoprecipitated with an antibody to the flag epitope tag and co-precipitating GST-SHP1-SH2 or GST-SHP2-SH2 was visualized with an anti-GST antibody.

The above assays revealed the following results. GST-SHP2-SH2 bound specifically to the phosphopeptide and not to other, nonspecific peptides (FIG. 6). GST-SHP1-SH2 bound to both the OB-R and EPOR phosphopeptides, indicating SHP1 has the ability to bind both OB-R and EPOR (FIG. 6). It did not bind to the nonspecific IFNγRα or IL-4Rα phosphopeptides (FIG. 6).

Figure 7:
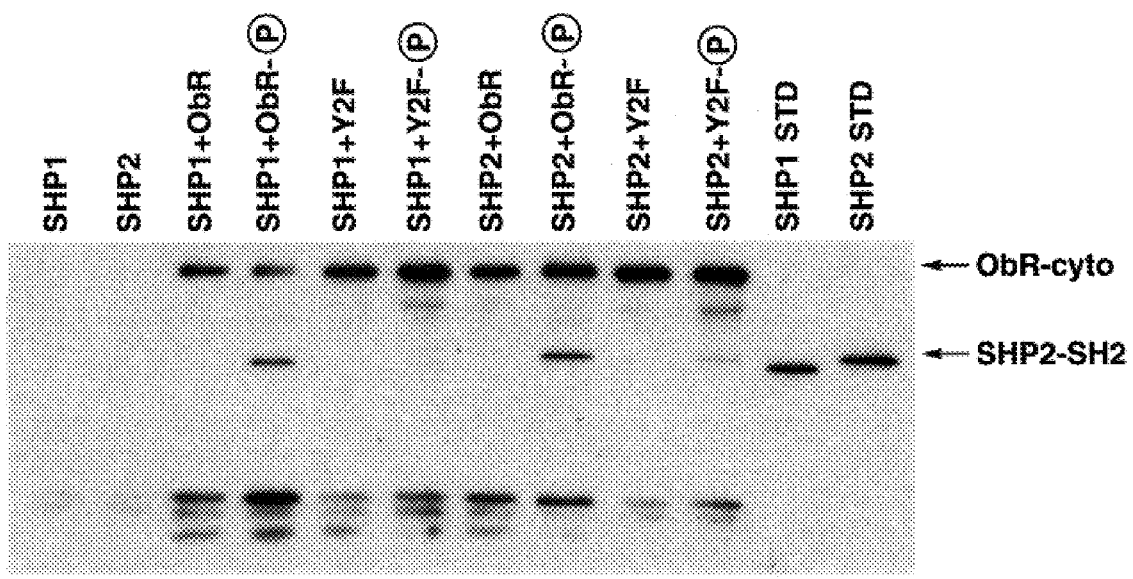
FIG. 7. GST-SHP1-SH2 or GST-SHP2-SH2 binding only to phosphorylated OB-R cytoplasmic domain. GST-SHP1-SH2 or GST-SHP2-SH2 was incubated with native or Y986F mutant OB-R cytoplasmic domain-GST fusions, either unphosphorylated (OB-R) or phosphorylated (OB-R-P). OB-R cytoplasmic domain fusion proteins were immunoprecipitated with an antibody to the myc epitope tag, and co-precipitating GST-SHP1-SH2 or GST-SHP2-SH2 was visualized with an anti-GST antibody (Sigma, St. Louis, Mo). The position of the GST-SHP2-SH2 is indicated, and GST-SHP1-SH2 lies just below.

GST-SHP2-SH2 and GST-SHP1-SH2 bound to the phosphorylated GST-OB-R-cyto and not to unphosphorylated GST-OB-R-cyto (FIG. 7). A mutation of the second tyrosine (amino acid 986 of OB-R) in GST-OB-R-cyto/myc significantly decreased the amount of GST-SHP2-SH2 and GST-SHP1-SH2 that coprecipitated with the phosphorylated GST-OB-R-cyto/myc (FIG. 7). Both the mutant and wild-type forms of GST-OB-R-cyto were phosphorylated similarly. This indicated that both SHP1-SH2 and SHP2-SH2 required the second phospho-tyrosine of OB-R for binding.

Figure 8:
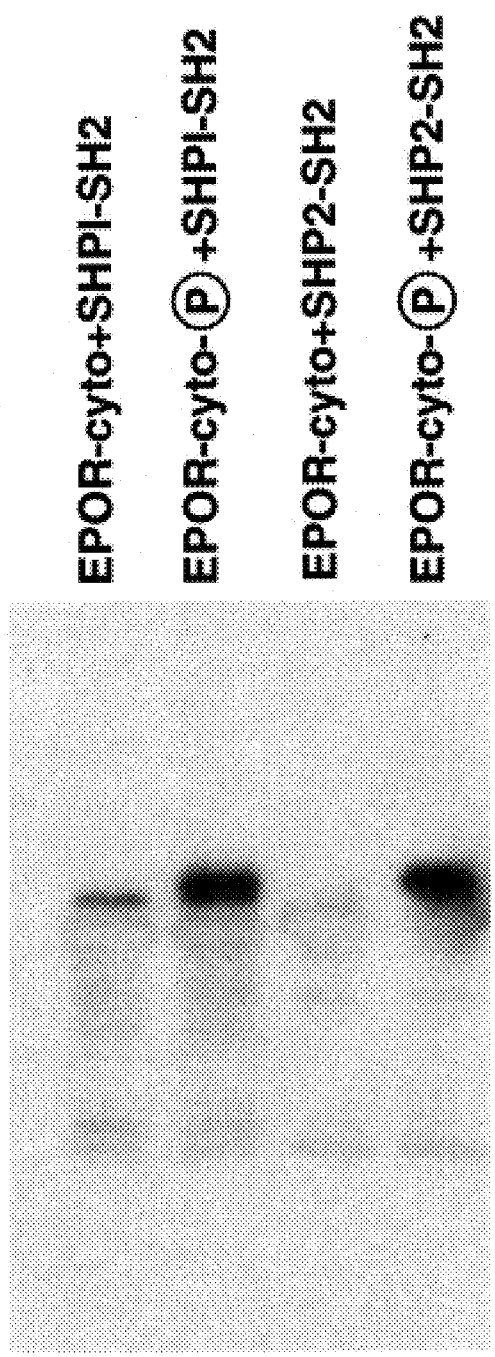
FIG. 8. GST-SHP1-SH2 or GST-SHP2-SH2 binding only to phosphorylated EPOR cytoplasmic domain. GST-SHP1-SH2 or GST-SHP2-SH2 was incubated with EPOR cytoplasmic domain-Trx fusions, either unphosphorylated or phosphorylated (EPOR-cyto-P). GST-SHP1-SH2 or GST-SHP2-SH2 were immunoprecipitated with an antibody to GST and co-precipitating EPOR cytoplasmic domain fusion protein was visualized with an anti-Trx antibody (Sigma, St. Louis, Mo.).

Both GST-SHP2-SH2 and GST-SHP1-SH2 bound with a higher affinity to the phosphorylated EPOR-cyto-Trx fusion than to the unphosphorylated fusion (FIG. 8).

Figure 9:
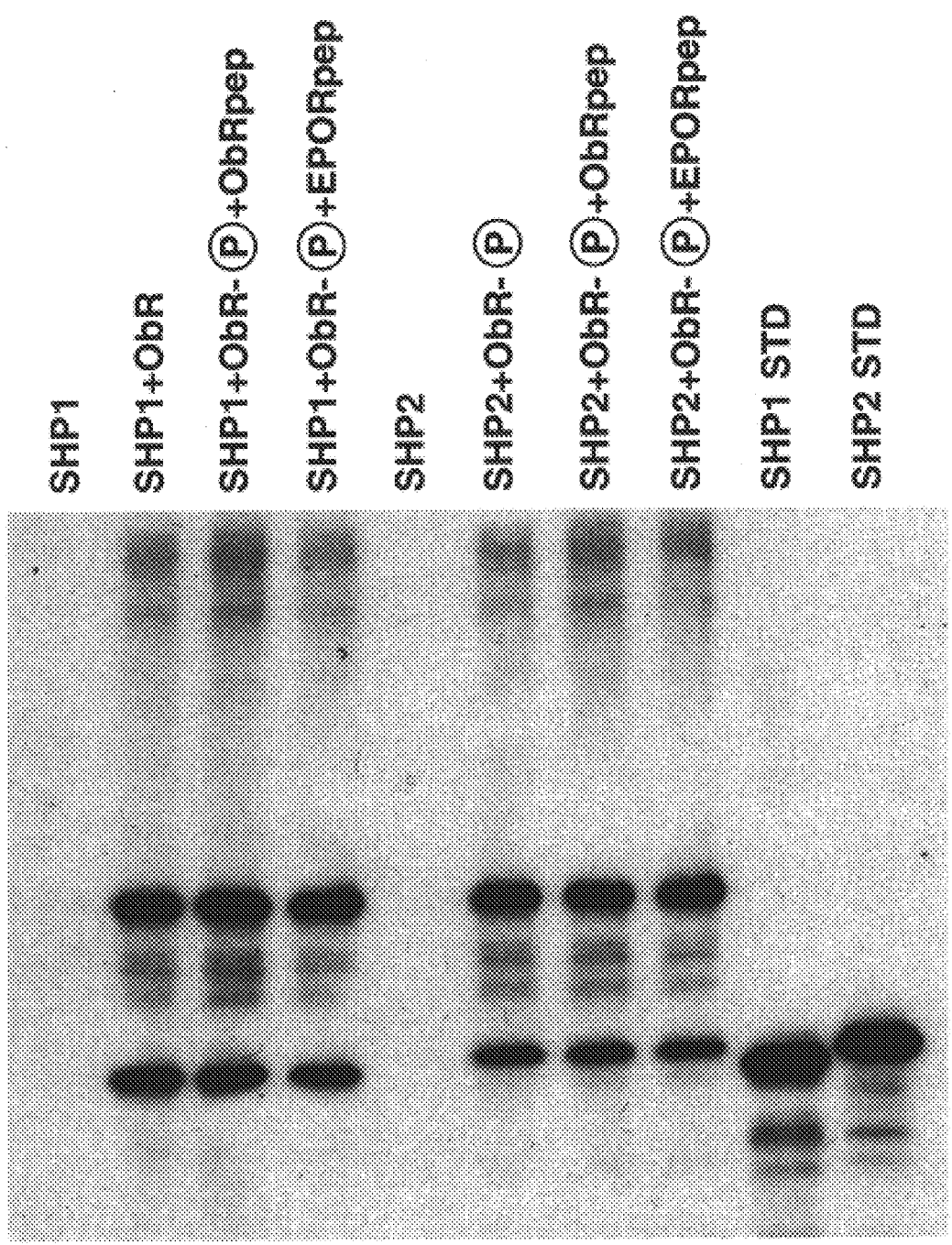
FIG. 9. Competition for GST-SHP1-SH2 or GST-SHP2-SH2 binding to OB-R-cyto-P by a phosphopeptide containing the sequence surrounding Y986 in OB-R. 200 nM GST-SHP1-SH2 or GST-SHP2-SH2, 15 nM OB-R-cyto-P, with and without 4 μM peptide were incubated together. OB-R-cyto-P was immunoprecipitated with an antibody to the myc epitope tag, and co-precipitating GST-SHP1-SH2 or GST-SHP2-SH2 was visualized with an anti-GST antibody.

We attempted to compete binding of GST-OB-R-cyto/3myc and GST-SHP2-SH2 or GST-SHP1-SH2 with 4 µM phosphopeptide and saw no competition (the cytoplasmic domain concentration was 15 nM, 266 fold less than the peptide) (FIG. 9). In this experiment the SH2 domain, the cytoplasmic domain, and the peptide were mixed and allowed to reach equilibrium. The receptor cytoplasmic domain was precipitated with anti-myc mAb and complexed GST-SHP1-SH2 and GST-SHP2-SH2 were detected by western blot with an anti-GST antibody.

Figure 10:
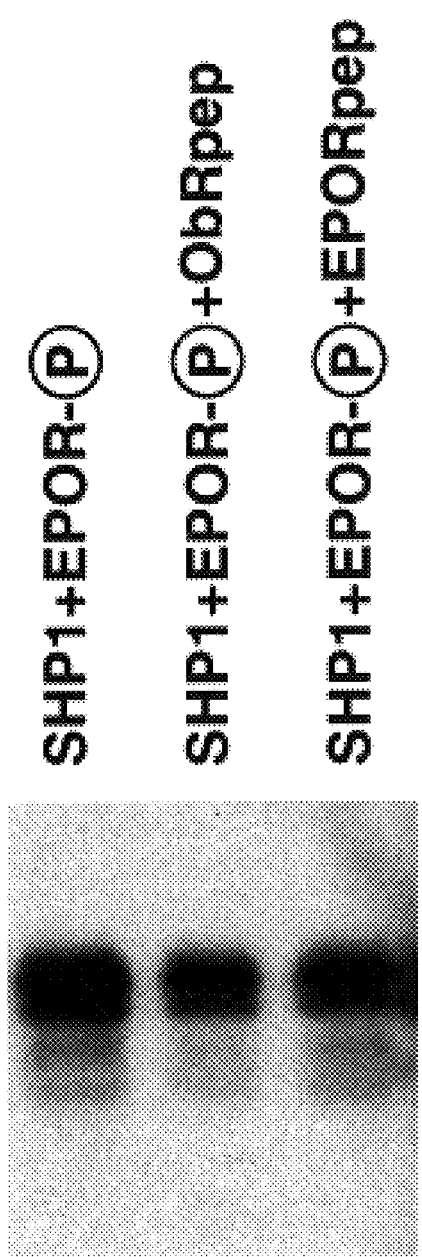
FIG. 10. Competition for GST-SHP1-SH2 or GST-SHP2-SH2 binding to EPOR-cyto-P by a phosphopeptide derived from the sequence surrounding Y401 of the cytoplasmic domain of the EPO receptor. 200 nM GST-SHP1-SH2 or GST-SHP2-SH2, 15 nM EPOR-cyto-P, with and without 4

A similar competition of EPOR-cyto-Trx with EPOR or OB-R phosphopeptide for GST-SHP1-SH2 binding showed a small amount of competition, but the phosphopeptides were not able to fully compete for binding (FIG. 10). In this competition the complexes were precipitated with glutathione-sepharose and the EPOR-cyto-Trx was detected by western blot using anti-Trx antibodies. The results from these experiments indicate that there may be higher binding affinity of the SH2 domains with the full receptor cytoplasmic domains than with the phosphopeptides, possibly because of secondary and tertiary structures the proteins have that the phosphoproteins lack.

Similar results were obtained utilizing the TrkC-OB-R chimeric receptors transiently transfected into neuroblastoma cells (NBFL). Activation of TOBR resulted in ~8-fold increase in luciferase activity whereas expression of TOBRY986F gave ~45-fold increase (FIG. 11). Thus, abrogation of SHP-2 activation by mutating tyrosine Y986 in OB-R results in an upregulation of STAT3-mediated signaling upon OB-R activation.

Upregulation of STAT3-mediated gene transcription in cells expressing OB-RY986F could be explained if SHP-2 normally functioned to directly dephosphorylate STAT3, and the receptor mutation preventing SHP-2 activation resulted in elevated or prolonged levels of STAT3 tyrosine phosphorylation. We therefore examined a timecourse of STAT3 tyrosine phosphorylation, using an antibody specific for phosphotyrosine at amino acid 705, following leptin activation of either native OB-R or mutant OB-RY986F. At 10 minutes, STAT3 is tyrosine phosphorylated to similar levels in cells expressing either native OB-R or mutant OB-RY986F (FIG. 5B, lane 4 and 10, respectively), and shows comparable rates of disappearance over 5 hours for both receptors (FIG. 5B, lane 8 and 14, respectively). The total amount of receptor tyrosine phosphorylation is lower for OB-RY986F than OB-R despite similar levels of receptor expression (data not shown) due to the replacement of tyrosine 986 with phenylalanine. However, the relative rates of disappearance of receptor tyrosine phosphorylation for OB-R and OB-RY986F were similar, with a maximum at 10 minutes (FIG. 5A, lanes 4 and 11, respectively) and detection of phosphorylated receptor for up to 1 hour (FIG. 5A, lanes 6 and 12, respectively). Tyrosine phosphorylation of receptor-associated jak was also observed (FIG. 5A), and followed a similar rate of disappearance as receptor phosphorylation, though the overall amount appears slightly lower at 30 minutes for OB-RY986F (FIG. 5A, compare lanes 5 and 11). These results indicate that there is no large difference in the tyrosine phosphorylation state or duration for either receptor, Jak or STAT3 between cells expressing native OB-R and mutant OB-RY986F. Thus, direct dephosphorylation of receptor, receptor-associated Jak, or STAT3 does not appear to be the mechanism by which SHP-2 downregulates STAT3-mediated gene transcription upon leptin stimulation of OB-R.

REFERENCES

1. Zhang, Y., Proenca, R., Maffei, M., Barone, M., Leopold, L. & Friedman, J. M. (1994) *Nature* 372, 425–431
2. Tartaglia, L. A., Dembski, M., Weng, X., Deng, N., Culpepper, J., Devos, R., Richards, G. J., Campfield, L. A., Clark, F. T., Deeds, J., Muir, C., Sanker, S., Moriarty, A., Moore, K. J., Smutko, J. S., Mays, G. G., Woolf, E. A., Monroe, C. A. & Tepper, R. I. (1995) *Cell* 83, 1263–1271
3. Coleman, D. L. (1978) *Diabetologia* 14, 141–148
4. Considine, R. V., Considine, E. L., Williams, C. J., Nyce, M. R., Magosin, S. A., Bauer, T. L., Rosato, E. L., Colberg, J. & Caro, J. F. (1995) *J. Clin. Invest.* 95,2986–2988
5. Considine, R. V., Considine, E. L., Williams, C. J., Hyde, T. M. & Caro, J. F. (1996) *Diabetes* 19, 992–994
6. Pelleymounter, M. A., Cullen, M. J., Baker, M. B., Hecht, R., Winters, D., Boone, T. & Collins, F. (1995) *Science* 269, 540–543
7. Halaas, J. L., Gajiwala, K. S., Maffei, M., Cohen, S. L., Chait, B. T., Rabinowitz, D., Lallone, R. L., Burley, S. K. & Friedman, J. M. (1995) *Science* 269, 543–546
8. Campfield, L. A., Smith, F. J., Guisez, Y., Devos, R. & Burn, P. (1995) *Science* 269, 546–549
9. Maffei, M., Halaas, J., Ravussin, E., Pratley, R. E., Lee, G. H., Zhang, Y., Fei, H., Kim, S., Lallone, R., Ranganathan, S., Kern, P. A. & Friedman, J. M. (1995) *Nature Med.* 1, 1155–1161
10. Considine, R. V., Sinha, M. K., Heiman, M. L., Kriauciunas, A., Stephens, T. W., Nyce, M. R., Ohannesian, J. P., Marco, C. C., McKee, L. J., Bauer, T. L. & Caro, J. F. (1996) *N. Engl. J. Med.* 334, 292–295
11. Sinha, M. K., Opentabova, I., Ohannesian, J. P., Kolaczynski, J. W., Heiman, M. L., Hale, J., Becker, G. W., Bowsher, R. R., Stephens, T. W. & Caro, J. F. (1996) *J. Clin. Invest.* 98, 1277–1282
12. Flier, J. S. & Elmquist, J. K. (1997) *Nature Biotech.* 15, 20–21
13. Campfield, L. A., Smith, F. J. & Burn, P. (1996) *Horm. Metab. Res.* 28, 619–632
14. Caro, J. F., Kolaczynski, J. W., Nyce, M. R., Ohannesian, J. P., Opentanova, I., Goldman, W. H., Lynn, R. B., Zhang, P. -L., Sinha, M. K. & Considine, R. V. (1996) *Lancet* 348, 159–161
15. Madej, T., Boguski, M. S. & Bryant, S. H. (1995) *FEBS Lett.* 373, 13–18
16. Kishimoto, T., Akira, S. & Taga, T. (1992) *Science* 258, 593–597
17. Stahl, N. & Yancopoulos, G. D. (1994) *J. Neurobiology* 25, 1454–1466
18. Stahl, N., Boulton, T. G., Farruggella, T., Ip, N. Y., Davis, S., Witthuhn, B., Quelle, F. W., Silvennoinen, O., Barbieri, G., Pellegrini, S., Ihle, J. N. & Yancopoulos, G. D. (1994) *Science* 263, 92–95
19. Lutticken, C., Wegenka, U. M., Yuan, J., Buschmann, J., Schindler, C., Ziemiecki, A., Harpur, A. G., Wilks, A. F., 19. Yasukawa, K., Taga, T., Kishimoto, T., Barbieri, G., Pellegrini, S., Sendtner, M., Heinrich, P. C. & Horn, F. (1994) *Science* 263, 89–92
20. Stahl, N., Farrugella, T. J., Boulton, T. G., Zhong, Z., Darnell, J. E. & Yancopoulos, G. D. (1995) *Science* 267, 1349–1353
21. Lee, G. -H., Proenca, R., Montez, J. M., Carroll, K. M., Darvishzadeh, J. G., Lee, J. I. & Friedman, J. M. (1996) *Nature* 379, 632–635
22. Chen, H., Charlat, O., Tartaglia, L. A., Woolf, E. A., Weng, X., Ellis, S. J., Lakey, N. D., Culpepper, J., Moore, K. J., Breitbart, R. E., Duyk, G. M., Tepper, R. I. & Morgenstern, J. P. (1996) *Cell* 84, 491–495
23. Cioffi, J. A., Shafer, A. W., Zupancic, T. J., Smith-Gbur, J., Mikhail, A., Platika, D. & Snodgrass, H. R. (1996) *Nature Med.* 2, 585–593
24. Wang, M. Y., Zhou, Y. T., Newgard, C. B. & Unger, R. H. (1996) *FEBS Lett.* 392, 87–90
25. Ghilardi, N., Ziegler, S., Wiestner, A., Stoffel, R. & Heim, M. H. (1996) *Proc. Natl. Acad. Sci. USA* 93, 6231–6235
26. Baumann, H., Morell, K. K., White, D. W., Dembski, M., Bailon, P. S., Kim, H., Lai, C. -F. & Tartaglia, L. A. (1996) *Proc. Natl. Acad. Sci. USA* 93, 8374–8378
27. Rosenblum, C. I., Tota, M., Cully, D., Smith, R., Collum, R., Qureshi, S., Hess, J. F., Phillips, M. S., Hey, P. J., Vongs, A., Fong, R. M., Xu, L., Chen, H. Y., Smith, R. G., Schindler, C. & Van der Ploeg, L. H. T. (1996) *Endocrinology* 137, 5178–5181
28. Vaisse, C., Halaas, J. L., Horvath, C. M., Darnell, J. E., Stoffel, M. & Friedman, J. M. (1996) *Nature Gen.* 14, 95–97
29. White, D. W., Kuropatwinski, K. K., Devos, R., Baumann, H. & Tartaglia, L. A. (1997) *J. Biol. Chem* 272, 4065–4071
30. Symes, A., Lewis, S., Corpus, L., Rajan, P., Hyman, S. E. & Fink, J. S. (1994) *Mol. Endocrin.* 8, 1750–1763
31. Baumann, H., Symes, A. J., Comeau, M. R., Morella, K. K., Wang, Y., Friend, D., Ziegler, S. F., Fink, J. S. & Gearing, D. P. (1994) *Mol. Cell. Biol.* 14, 138–146
32. Songyang, Z., Shoelson, S. E., Chaudhuri, M., Gish, G., Pawson, T., Haser, W. G., King, F., Roberts, T., Ratnofsky, S., Lechleider, R. J., Neel, B. G., Birge, R. B., Fajardo, J. E., Chou, M. M., Hanafusa, H., Schaffhausen, B. & Cantley, L. C. (1993) *Cell* 72, 767–778.
33. Tauchi, T., Damen, J. E., Toyama, K., Feng, G. -S., Broxmeyer, H. E. & Krystal, G. (1996) *Blood* 87, 4495–4501
34. Klingmuller, U., Lorenz, U., Cantley, L. C., Neel, B. G. & Lodish, H. F. (1995) *Cell* 80, 729–738
35. Yi, T., Mui, A. L. -F., Krystal, G. & Ihle, J. N. (1993) *Mol. Cell. Biol.* 13, 7577–7586
36. D'Ambrosio, D., Hippen, K. L., Minskoff, S. A., Mellman, I., Pani, G., Siminovitch, K. A. & Cambier, J. C. (1995) *Science* 268, 293–297
37. Shultz, L. D., Schweitzer, P. A., Rajan, T. V., Yi, T., Ihle, J. N., Matthews, R. J., Thomas, M. L. & Beier, D. R. (1993) *Cell* 73, 1445–1454
38. Ali, S., Chen, Z., Lebrun, J. -J., Vogel, W., Kharitonenkov, A., Kelly, P. A. & Ullrich, A. (1996) *EMBO J.* 15, 135–142
39. Lechleider, R. J., Freeman, R. M. & Neel, B. G. (1993) *J. Biol. Chem.* 268, 13434–13438
40. Li, W., Nishimura, R., Kashishian, A., Batzer, A. G., Kim, W. J., Cooper, J. A. & Schlessinger, J. (1994) *Mol. Cell. Biol.* 14, 509–517
41. Kharitonenkov, A., Schnekenburger, J., Chen, Z., Knyazev, P., Sli, S., Zwick, E., White, M. & Ullrich, A. (1995) *J. Biol. Chem.* 270, 29189–29193
42. David, M., Zhou, G., Pine, R., Dixon, J. E. & Larner, A. C. (1996) *J. Biol. Chem.* 271, 15862–15865
43. Fukuda, T., Hibi, M., Yamanaka, Y., Takahasi-Tezuka, M., Fujitani, Y., Tamaguchi, T., Nakajima, K. & Hirano, T. (1996) *Immunity* 5, 449–460
44. Marengere, L. E. M., Waterhouse, P., Duncan, G. S., Mittrucker, H. -W., Feng, G. -S. & Mak, T. W. (1996) *Science* 272, 1170–1173
45. de la Chapelle, A., Traskelin, A. -L. & Juvonen, E. (1993) *Proc. Natl. Acad. Sci. USA* 90, 4495–4499
46. Endo, T. A., Masuhara, M., Yokouchi, M., Suzuki, R., Sakamoto, H., Mitsui, K., Matsumoto, A., Tanimura, S., Ohtsubo, M., Misawa, H., Miyazaki, T., Leonor, N., Taniguchi, T., Fujita, T., Kanakura, Y., Komiya, S. &
47. Naka, T., Narazaki, M., Hirata, M., Matsumoto, T., Minamoto, S., Aono, A., Nishimoto, N., Kajita, T., Taga, T., Yoshizaki, K., Akira, S. & Kishimoto, T. (1997) *Nature* 387, 924–928.
48. Starr, R., Willson, T. A., Viney, E. M., Murray, L. J. L., Rayner, J. R., Jenkins, B. J., Gonda, T. J., Alexander, W. S., Metcalf, D., Nicola, N. A. & Hilton, D. J. (1997) *Nature* 387, 917–921.
49. ALS CNTF Treatment Study Group (1996) *Neurology* 46, 1244–1249.
50. Gloagen, I., Costa, P., Demartis, A., Lazzaro, D., Di Marco, A., Graziani, R., Paonessa, G., Chen, F., Rosenblum, C. I., Van der Ploeg, L. H. T., Cortese, R., Ciliberto, G. & Laufer, R. (1997) *Proc. Natl. Acad. Sci (USA)* 94, 6456–6461.
51. Symes, A., Stahl, N., Reeves, S. A., Farruggella, T., Servidei, T., Gearan, T., Yancopoulos, G. D. & Fink, J. S. (1997) *Curr. Biol.* 7, 697–700.
52. Servidei, T., Aoki, Y., Lewis, S. E., Symes, A., Fink, J. S. & Reeves, S. A. (1998) *J. Biol. Chem.* 273, 6233–6241.

We claim:

1. A method of screening for a molecule capable of competing with OB-R for binding to Src homology 2 containing protein tyrosine phosphatase 2 (SHP-2) comprising:
   a) contacting an OB-R phosphopeptide comprising the Y986 domain of the OB-R of SEQ ID NO: 1 under conditions in which the OB-R phosphopeptide is capable of binding to an SHP-2-SH2 peptide comprising src homology domain 2 of SHP-2;
   b) determining the amount of the OB-R phosphopeptide that binds to the SHP-2-SH2 peptide;
   c) contacting a known amount of the OB-R phosphopeptide to the SHP-2-SH2 peptide, in the presence of a sample suspected of containing the molecule capable of competing with the OB-R phosphopeptide, under the same conditions used in b);
   d) determining the amount of the OB-R phosphopeptide that binds to the SHP-2-SH2 peptide; and
   e) comparing the amount from (b) with the amount from (d), wherein a lesser amount in (d) indicates the presence of a molecule capable of competing with the OB-R phosphopeptide for binding to the SHP-2-SH2 peptide.

2. The method of claim 1, wherein the OB-R phosphopeptide or the SHP-2-SH2 peptide is bound to a solid support.

3. The method of claim 2, wherein the OB-R phosphopeptide or the SHP-2-SH2 peptide is detectably labeled.

4. The method of claim 1 wherein the OB-R phosphopeptide is the cytoplasmic domain of the OB-R (amino acids 865–1165 of of SEQ ID NO: 1.

5. The method of claim 1 wherein the OB-R phosphopeptide is a dimer.

* * * * *